(12) United States Patent
Abrams et al.

(10) Patent No.: US 8,303,616 B2
(45) Date of Patent: Nov. 6, 2012

(54) INTERNAL RESTRAINT FOR DELIVERY OF SELF-EXPANDING STENTS

(75) Inventors: Robert M. Abrams, Los Gatos, CA (US); Elaine Lee, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2580 days.

(21) Appl. No.: 11/028,808

(22) Filed: Jan. 3, 2005

(65) Prior Publication Data

US 2005/0143773 A1 Jun. 30, 2005

Related U.S. Application Data

(62) Division of application No. 09/950,158, filed on Sep. 10, 2001, now abandoned.

(51) Int. Cl.
*A61M 29/00* (2006.01)
(52) U.S. Cl. ........................................ 606/198; 623/1.11
(58) Field of Classification Search .................. 606/191, 606/192, 194, 195, 198, 108; 623/1.11, 1.12, 623/1.15, 1.21, 1.23
See application file for complete search history.

(56) References Cited

U.S. PATENT DOCUMENTS

| | | | | |
|---|---|---|---|---|
| 4,913,141 A * | 4/1990 | Hillstead | ...................... | 623/1.11 |
| 5,261,878 A | 11/1993 | Galindo | ...................... | 604/103.1 |
| 5,405,378 A * | 4/1995 | Strecker | ...................... | 623/1.12 |
| 5,542,926 A | 8/1996 | Crocker | ...................... | 604/102.02 |
| 5,571,135 A | 11/1996 | Fraser et al. | ...................... | 606/198 |
| 5,693,083 A * | 12/1997 | Baker et al. | ...................... | 623/1.11 |
| 5,776,141 A | 7/1998 | Klein et al. | ...................... | 606/108 |
| 6,059,813 A | 5/2000 | Vrba et al. | ...................... | 606/198 |
| 6,090,115 A | 7/2000 | Beyar et al. | ...................... | 606/113 |
| 6,117,140 A | 9/2000 | Munsinger | ...................... | 606/108 |
| 6,120,522 A | 9/2000 | Vrba et al. | ...................... | 606/190 |
| 6,179,878 B1 | 1/2001 | Duerig et al. | ...................... | 128/89 B |
| 6,203,558 B1 | 3/2001 | Dusbabek et al. | ...................... | 606/198 |
| 6,206,888 B1 | 3/2001 | Bicek et al. | | |
| 6,254,609 B1 | 7/2001 | Vrba et al. | ...................... | 606/108 |
| 6,254,611 B1 | 7/2001 | Vrba | ...................... | 606/108 |
| 6,398,802 B1 * | 6/2002 | Yee | ...................... | 623/1.13 |
| 6,468,301 B1 | 10/2002 | Amplatz et al. | ...................... | 623/1.13 |
| RE38,091 E | 4/2003 | Strecker | ...................... | 623/1.12 |
| 2001/0003297 A1 | 6/2001 | Pedersen et al. | ...................... | 156/298 |
| 2001/0012959 A1 * | 8/2001 | Blaeser et al. | ...................... | 623/1.11 |
| 2001/0027323 A1 | 10/2001 | Sullivan, III et al. | ...................... | 606/108 |
| 2001/0034547 A1 | 10/2001 | Hall et al. | ...................... | 623/1.11 |
| 2001/0034548 A1 | 10/2001 | Vrba et al. | ...................... | 623/1.11 |
| 2002/0029077 A1 * | 3/2002 | Leopold et al. | ...................... | 623/1.11 |
| 2003/0009174 A1 * | 1/2003 | Smith | ...................... | 606/108 |
| 2003/0023298 A1 * | 1/2003 | Jervis | ...................... | 623/1.11 |
| 2003/0028237 A1 * | 2/2003 | Sullivan et al. | ...................... | 623/1.11 |

(Continued)

FOREIGN PATENT DOCUMENTS

DE 4137857 5/1992

(Continued)

*Primary Examiner* — S. Thomas Hughes
*Assistant Examiner* — Julie A Szpira
(74) *Attorney, Agent, or Firm* — Vidas, Arrett and Steinkraus

(57) ABSTRACT

A medical device delivery system comprises a catheter having a catheter shaft with a proximal region and a distal region. The catheter shaft has a pull wire lumen therein. An expandable medical device is disposed about medical device receiving region of the catheter shaft. The expandable medical device has a reduced configuration and an expanded configuration. The system further comprises a retractable retaining wire, at least a portion of which is coiled about the expandable medical device and retains the expandable medical device in the reduced configuration. One end of the retractable retaining wire terminates in a pull-wire. The pull-wire extends into the pull-wire lumen to the proximal region of the catheter shaft.

13 Claims, 5 Drawing Sheets

FOREIGN PATENT DOCUMENTS

| | | |
|---|---|---|
| EP | 0696447 A2 | 2/1996 |
| WO | 94/22379 | 10/1994 |
| WO | 96/13228 | 5/1996 |
| WO | 01/41676 | 6/2001 |
| WO | 01/64134 | 9/2001 |

* cited by examiner

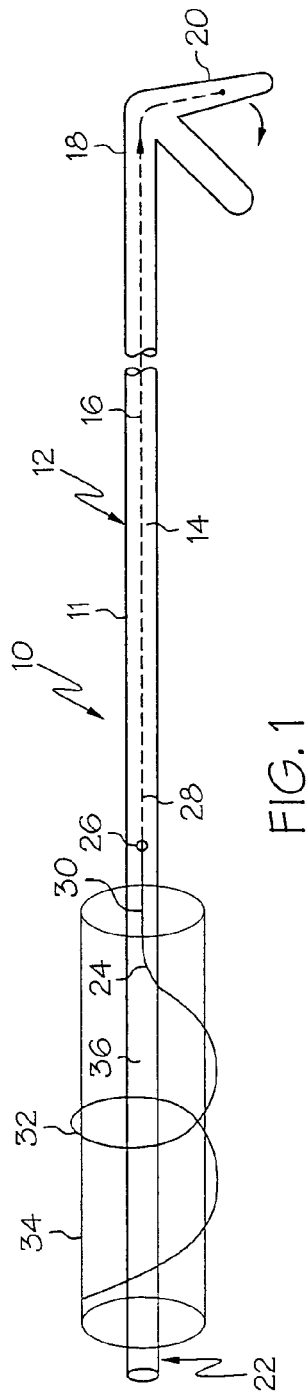
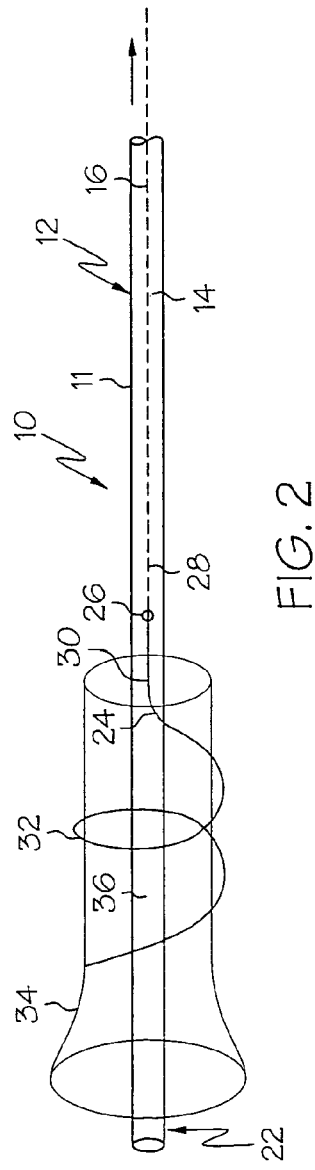
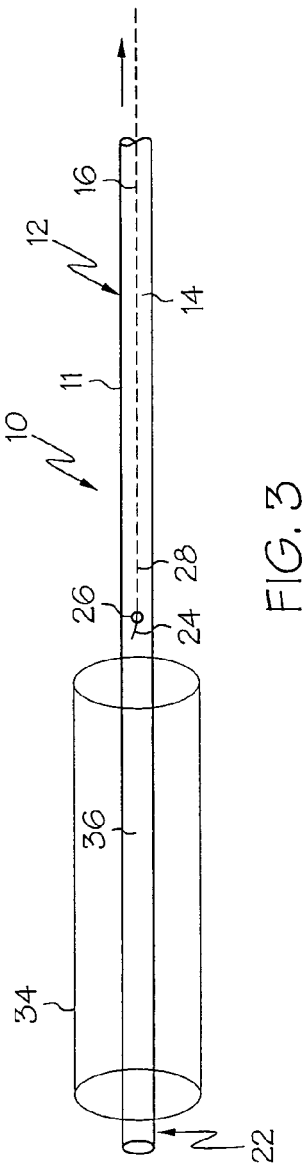

INTERNAL RESTRAINT FOR DELIVERY OF SELF-EXPANDING STENTS

CROSS-REFERENCE TO RELATED APPLICATIONS

This application is a divisional application of U.S. application Ser. No. 09/950,158, which was filed Sep. 10, 2001, the entire contents of which is incorporated herein by reference.

BACKGROUND OF THE INVENTION

Stents are used in a wide variety of locations in the body including in coronary arteries, renal arteries, peripheral arteries including iliac arteries, arteries of the neck and cerebral arteries. Stents are also used in other bodily locations including but not limited to arteries, veins, biliary ducts, urethras, fallopian tubes, bronchial tubes, the trachea, the esophagus and the prostate.

Stents typically are self-expanding, balloon expandable or a hybrid of the two. Self-expanding stents may be made of shape memory metals such as nitinol, shape memory polymer materials, or constructed of non-shape memory metals but of a design which exhibits self-expansion characteristics. Balloon expandable stents are typically delivered on a balloon and the balloon is used to the expand the stent. Hybrid stents have both self-expanding properties and balloon expanding properties.

Typically, stents are delivered to desired bodily locations via the use of catheters. A catheter comprising a stent is introduced into a bodily vessel and advanced through the vasculature in the body until the stent is positioned in a desired location. Usually, the stent will be protected by a retractable sheath which is disposed about the stent and which increases the profile of the delivery catheter. The sheath may be removed from about the stent via the use of a retraction device such as a pull-wire, pull rod or a catheter tube which is connected to the sheath. As part of the removal, the sheath may optionally be rolled off of the stent. In the case of self-expanding stents, the sheath may also restrain the stent from self-expanding. Once at the desired location, the stent is either allowed to self-expand or is balloon expanded. In the case of self-expanding stents, the self-expansion may occur as a result of the removal of the sheath from about the stent.

Unfortunately, many self-expanding stent delivery systems, in particular those using retractable sheaths, employ cumbersome and/or bulky deployment mechanisms.

There remains a need for medical device delivery systems in general and stent delivery systems in particular which avoid the use of cumbersome and/or bulky deployment mechanisms.

There also is a need for expandable medical devices which are capable of being retained on a catheter with a retractable retaining member of minimal profile.

The entire content of all of the patents listed within the present patent application are incorporated herein by reference.

The invention in various of its embodiments is summarized below. Additional details of the invention and/or additional embodiments of the invention may be found in the Detailed Description of the Invention below. An abstract of one of the embodiments of the invention is also provided below.

SUMMARY OF THE INVENTION

In one embodiment, the present invention is directed to a delivery system for delivering a medical device to a location in a body lumen. The delivery system comprises a catheter having a catheter shaft with a proximal region and a distal region. The catheter shaft has a pull wire lumen therein. At least a portion of the distal region defines a medical device receiving region. An expandable medical device is disposed about the medical device receiving region. The expandable medical device has a reduced configuration and an expanded configuration. The system further comprises a retractable retaining wire, at least a portion of which is coiled about the expandable medical device and retains the expandable medical device in the reduced configuration. The wire may be characterized as a ribbon or may have other shapes and configurations. One end of the retractable retaining wire terminates in a pull-wire. The pull-wire extends into the pull-wire lumen to the proximal region of the catheter shaft.

In another embodiment, the invention is directed to a medical device delivery system comprising a catheter having an outer member and a retractable inner member. The catheter has a proximal region and a distal region. At least a portion of the distal region of the inner member defines a medical device receiving region. An expandable medical device having a reduced configuration and an expanded configuration is disposed about the medical device receiving region of the inner member in the reduced configuration. The expandable medical device comprises a plurality of interconnected struts. One or more flexible members, each having a first end and a second end, are looped about the medical device receiving region of the inner member retaining the medical device in the reduced configuration. Each end of the flexible members is engaged to one or more struts.

In yet another embodiment, the invention is directed to an expandable medical device having a reduced configuration and being expandable to an expanded configuration. The expandable medical device comprises a plurality of interconnected struts which define an internal tubular passage. The expandable medical device further comprises one or more flexible members. Each of the one or more flexible members has a first end and a second end and extends into the internal tubular passage. Each end of the one or more flexible members is engaged to one or more struts.

In another embodiment, the invention is directed to a medical device delivery system comprising a catheter member having a proximal region and a distal region. At least a portion of the distal region of the catheter member defines a medical device receiving region. An expandable medical device having a reduced configuration and an expanded configuration, is disposed about the medical device receiving region of the catheter member in the reduced configuration. The expandable medical device further has one or more engagement members. Each engagement member has a first end and a second end. The first end is engaged to a location on the expandable medical device and the second end is releasably engaged to the medical device receiving region of the catheter member.

In another embodiment, the invention is directed to a medical device delivery system comprising a catheter member having a proximal region and a distal region. At least a portion of the distal region of the catheter member defines a medical device receiving region. An expandable medical device having a reduced configuration and an expanded configuration is disposed about the medical device receiving region of the catheter member in the reduced configuration. The system further comprises one or more engagement members, each having a first end and a second end. The first end of each engagement member is engaged to a location on the expandable medical device and the second end of each engagement member is engaged to a location on the medical device receiving region of the catheter member. The expandable medical device is expanded from the reduced configuration to the expanded configuration when the first ends of the engagement members are released from the expandable medical device or the second ends of the engagement members are released from the medical device receiving region.

In yet another embodiment, the invention is directed to an expandable medical device having a reduced configuration and being expandable to an expanded configuration. The expandable medical device comprises one or more engagement members, each of which has a first end and a second end. The first end of each of the engagement members is engaged to a location on the expandable medical device and the second end of each of the one or more engagement members extends radially inward from the first end. The engagement members are constructed and arranged to releasably engage a medical device receiving region of a catheter member.

The invention is also directed to methods of securing a medical device such as a stent to a catheter. In accordance with one inventive method, a stent is provided as is a catheter member. The catheter member may be in the form of a tube having a passage therethrough or in the form of a solid member. One or more engagement members, as disclosed above, extends from the stent and is releasably secured to the catheter member.

In accordance with another inventive method, one or more engagement members extending from the catheter member is releasably secured to the stent.

In yet another embodiment of the inventive methods, a stent having one or more flexible members, each having a first end secured to the stent and a second end secured to the stent, is provided. The flexible members form loops. A catheter member is inserted in the loops thereby retaining the stent in the reduced configuration.

A detailed description of the invention in its various embodiments is provided below.

BRIEF DESCRIPTION OF THE SEVERAL VIEWS OF THE DRAWINGS

A detailed description of the invention is hereafter described with specific reference being made to the drawings in which:

FIG. 1 is a side perspective view of an embodiment of the invention wherein a stent is shown retained about a delivery catheter by a retaining wire.

FIG. 2 is a side perspective view of the embodiment shown in FIG. 1 wherein the stent is shown expanding as a result of retraction of a retaining wire.

FIG. 3 is a side perspective view of the embodiment shown in FIG. 2 wherein the stent is shown expanded as a result of fully retracting the retaining wire from the stent;

DETAILED DESCRIPTION OF THE INVENTION

Figure 2A:
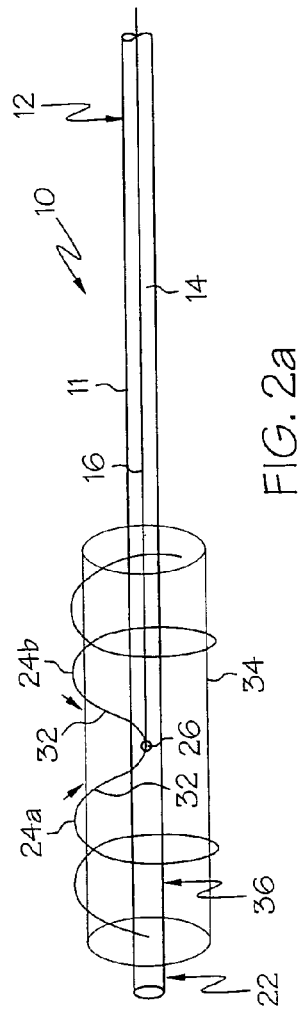
FIG. 2a is a side perspective view of an embodiment of the invention wherein a stent is shown retained about a delivery catheter by a pair of retaining wires extending from a single port.

While this invention may be embodied in many different forms, there are described in detail herein specific exemplary embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

As indicated above, the present invention is directed to novel expandable medical devices as well as their associated delivery systems.

In one embodiment of the invention such as is shown in FIG. 1 a delivery system, indicated generally at 10 is shown. Delivery system 10 includes a catheter 12. The catheter 12 may be any form of catheter suitable for the delivery of a medical device. In the embodiment shown, catheter 12 includes a shaft 11 which defines a lumen 14 through which a pull back wire 16 may move. Pull back wire 16 extends proximally to a proximal hub 18 of the catheter where it may be operated. Desirably, the pull back wire 16 terminates in an readily actuatable mechanism 20 which may be actuated to cause proximal retraction of the wire 16. An example of a suitable retraction mechanism 20 is described in U.S. Pat. No. 5,968,052, the entire contents of which is incorporated herein by reference.

At the distal region 22 of the catheter 12, the catheter comprises a retaining wire 24 which terminates in the pull back wire 16. The retaining wire 24 and pull back wire 16 may be of one piece construction or may be in the form of a retaining wire and a pull back wire which are welded, soldered or adhesively joined together. The retaining wire 24 may also be characterized as a wire of material.

The retaining wire 24 and pull back wire 16 combination exits the pull back wire lumen 14 through a port 26 in the side wall 28 of the catheter shaft 11. Where the wire 24 exits port 26, the wire 24 defines a relatively straight elongated proximal portion 30. The wire 24 may be readily drawn into the lumen 14 through port 26 when the pull back wire 16 is actuated.

The distal portion 32 of the wire 24 is coiled about an expandable medical device, such as a stent 34. The coiled portion of the wire retains the stent in a reduced profile configuration about a stent retaining area 36 of the catheter shaft 11. In the embodiment shown in FIG. 1, the stent 34 may be any type of stent including a self-expanding stent or a balloon expandable stent. Where the stent is balloon expandable or requires mechanical seating, the stent retaining area 36 of the catheter 12 may be or may include a medical balloon or other expansion device. Where the stent retaining area 36 includes a balloon, the catheter shaft 11 will include an inflation lumen or other means for inflating the balloon as is known in the art. The inflation lumen may be provided as part of catheter shaft 11.

In FIG. 2, the system 10 is shown during retraction of the wire 24. As the pull back wire 16 is proximally drawn, the wire 24 is retracted from about the stent 34 and into the lumen 14 through port 26. In the embodiment shown in FIG. 2, the stent 34 is a self-expanding stent and is shown expanding from the distal end as the wire 24 is withdrawn. As is shown in FIG. 3, once the wire 24 is withdrawn from about the stent 34, the stent is allowed to fully expand. Once stent 34 is fully expanded and positioned in the vessel, the catheter 12 may be withdrawn.

Depending on the location of the port 26, the wire 24 may be configured to be withdrawn from the proximal end or the distal end of the stent as desired. In another embodiment of the invention shown in FIG. 2*a*-2*b* multiple wires 24 may be provided through one or more ports to allow for simultaneous expansion of both ends of the stent or medial expansion as desired.

In FIG. 2*a* the system 10 is shown wherein a pair of retaining wires 24*a* and 24*b* are drawn through a single port 26. The wires 24*a* and 24*b* are retracted proximally through the lumen 14. However, depending on the position of the stent 34 relative to the port 26 portions of the wires 24*a* and/or 24*b* may be pulled distally as the wire(s) are drawn through the port 26 during retraction.

In the embodiment shown, the port 26 is positioned centrally in the stent retaining area 36. Where simultaneous retraction of both wires 24*a* and 24*b* is to be conducted, wires 24*a* and 24*b* may extend proximally to a single pull back wire 16. When the wires 24*a* and 24*b* are retracted the proximal and distal ends of the stent are initially exposed simultaneously before any other portion of the stent. By allowing the ends of the stent to be freed before the medial portion, the ends of the stent may be allowed to expand or begin expanding prior to the middle region of the stent.

Where it is desirable to permit a particular end of the stent 34 to expand before the other end, one of the wires 24*a* or 24*b* may be retracted first. In such an embodiment, each wire 24*a* and 24*b* must extend to a distinct and separate pull back wire, to allow for individualized retraction.

Figure 2B:
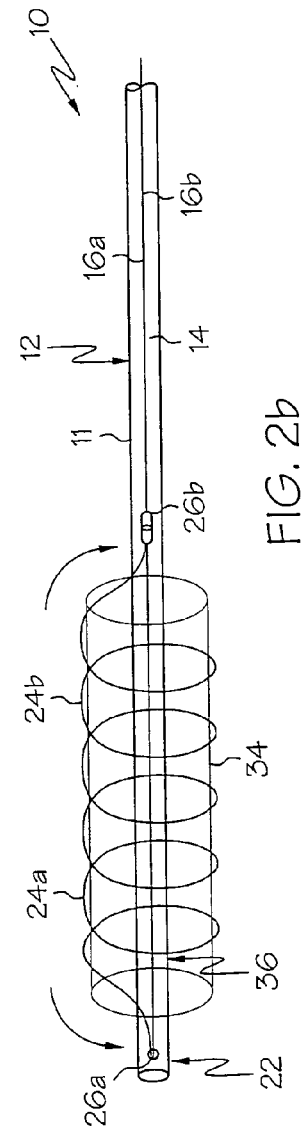
FIG. 2b is a side perspective view of an embodiment of the invention wherein a stent is shown retained about a delivery catheter by a pair of retaining wires with each wire extending from a respective port.

In another embodiment of the invention shown in FIG. 2*b*, the system 10 employs a pair of wires 24*a* and 24*b* each of which extends from a respective port 26*a* and 26*b*. Preferably, the ports 26*a* and 26*b* are positioned in the stent retaining area 36 such that when a stent 34 is placed thereabout, the wires 24*a* and 24*b* extend over the ends of the stent and are directed over the medial region of the stent. If the wires 24*a* and 24*b* are retracted simultaneously, the medial region of the stent is initially freed before the stent ends, thereby allowing the center of the stent to begin expansion prior to the ends.

Figure 4:
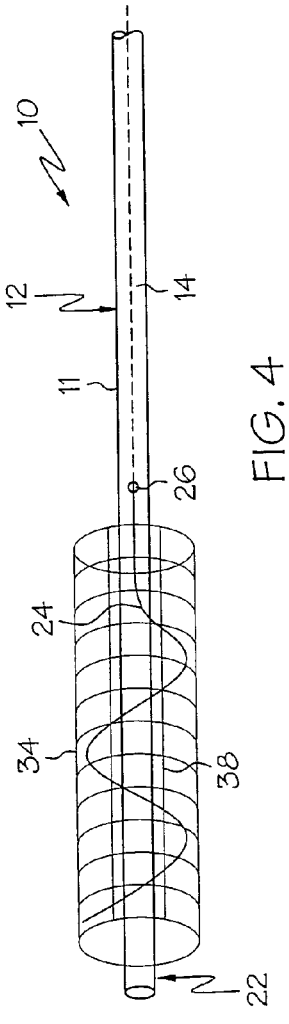
FIG. 4 is a side perspective view of an alternative embodiment of the invention wherein the retaining wire is threaded through the struts of the stent.

The number and placement of ports as well as wires may be varied as desired. The embodiments shown in FIGS. 2 and 2*a*-2*b* are merely examples of the wide range of configurations which may be embodied by the present invention. In addition to the number and position of the ports and wires, other embodiments may be employed such as the embodiment shown in FIG. 4, wherein the wire 24 may be threaded through selected struts 38 of the stent 24 to provide a more secure engagement of the stent in the reduced profile configuration. As the wire 24 is retracted, the wire 24 is un-threaded from the struts 38 as it is proximally withdrawn through the lumen 14.

In the embodiments shown in FIGS. 1-4, the wire(s) 24 may be constructed of any material capable of retaining a stent 34 in a reduced profile state, such as is shown in FIG. 1, but which is flexible enough to be readily withdrawn from the stent such as is shown in FIGS. 2 and 3. Optionally, to facilitate retraction of the wire 24 from the stent 34, the wire 24 may be constructed from a shape memory material such as nitinol and/or a shape memory polymer. Some examples of suitable shape memory polymers include but are not limited to: acrylate-based polymers, polyurethane-based polymers, polylactide-based polymers and polynorbornene based polymers.

The use of a shape memory material in wire 24 may provide the wire with the capability to uncoil from the stent 34 when the shape memory property is activated by a change in temperature, or pH in the wire 24 or surrounding area. The shape memory material may be temperature activated by the heat of the body or heat may be delivered to the wire 24 through the pull back wire 16. Alternatively, a warm saline bolus may be injected into the lumen 14 to increase the temperature surrounding the wire 24 prior to or during retraction. In one embodiment of the invention where the shape memory material of the wire 24 is pH activated, a bolus of pH-buffered saline may be injected into lumen 14 to change the pH of the area surrounding wire 24.

Figure 5:
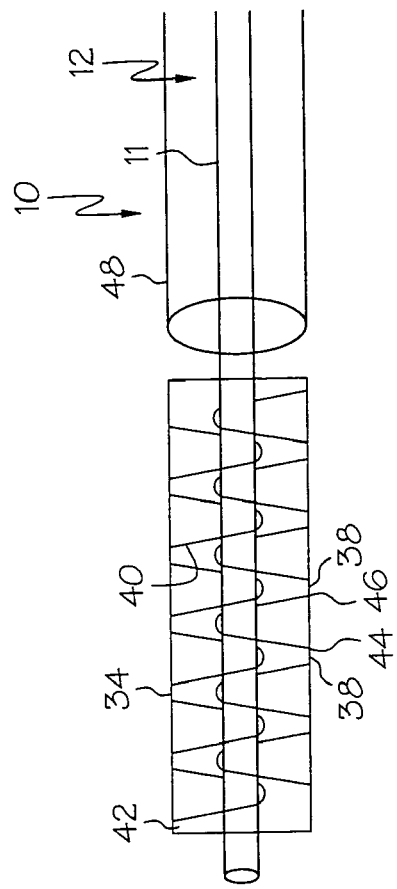
FIG. 5 is a side perspective view of an embodiment of the invention wherein a stent includes internal members for retaining the stent in a reduced configuration about a shaft of a delivery catheter.
Figure 6:
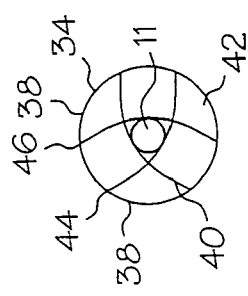
FIG. 6 is a cross-sectional view of the embodiment shown in FIG. 5.

Turning to FIGS. 5-6, another embodiment of the invention is shown wherein a self-expanding stent 34 is retained in the reduced profile configuration by internally mounted members 40 which engage the catheter shaft 11. The shaft 11 may be a solid member or may have one or more lumens therein, as desired. Members 40 extend between two ends 44 and 46. Ends 44 and 46 are each engaged to a strut 38 or other portion of the stent 34 in such a manner that when the member 40 is looped over the catheter shaft 11, the members retain the stent 34 in the reduced profile configuration and prevent the stent 34 from self-expanding. When multiple members 40 are distributed throughout the length of the stent interior 42 and engaged to the shaft 11, the stent 34 is drawn radially inward to the reduced profile configuration shown in FIGS. 5 and 6.

The members 40 may be any material which can be configured into strands suitable for placement within the lumen or interior 42 of a stent 34. In some embodiments of the invention, members 40 may be constructed from a material that can stretch elastically at least 50 percent of the original loop length, in a manner similar to that of a rubber band. Some examples of suitable elastic materials include but are not limited to silicone and/or polyurethane. Members 40 may be stretched around the shaft 11 prior to delivery of the stent 34.

Figure 7:
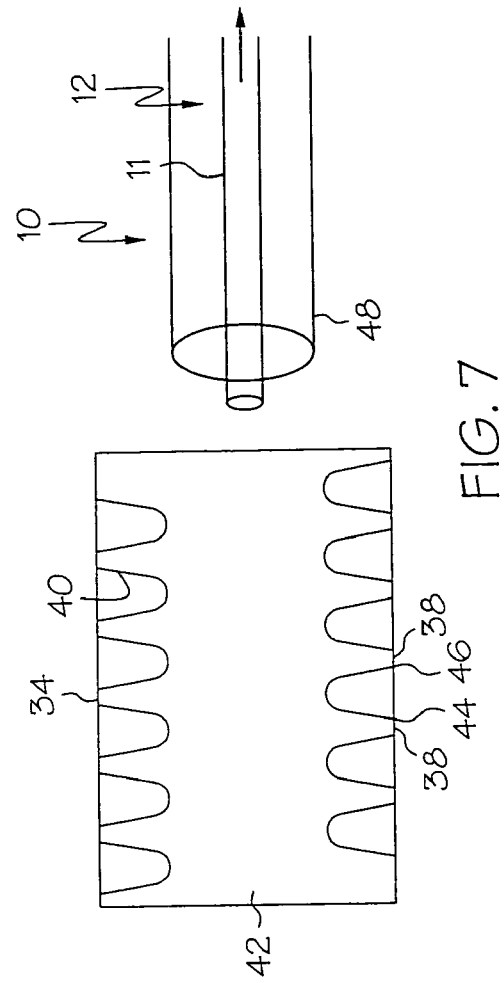
FIG. 7 is a side perspective view of the embodiment shown in FIG. 5, wherein the stent has been expanded by withdrawing the shaft from the retaining members.

In order to allow the stent 34 to self-expand, the shaft member 11 is withdrawn from the stent interior 42 as shown in FIG. 7. In some embodiments, the shaft 11 may be a wire or other elongate member. The shaft 11 and/or members 40 may be coated with a biocompatible lubricant to facilitate withdrawal of the shaft 11 from the interior 42. The catheter 12 includes a housing or other member 48 through which the shaft 11 may be withdrawn. The shaft 11 is capable of longitudinal movement relative to the housing 48. The housing 48, prevents the stent 34 from being shifted in position as the shaft 11 is withdrawn. After the shaft 11 is withdrawn from the stent interior 42, the entire catheter 12 including the housing 48 and shaft 11 may be withdrawn from the body. The invention also contemplates the use of other members adjacent to the catheter shaft 11 which can act to retain the stent 34 in place while the catheter shaft 11 is withdrawn.

Figure 8:
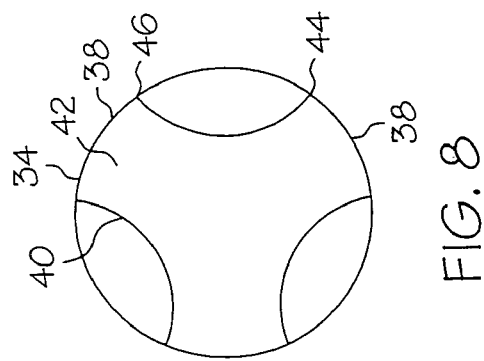
FIG. 8 is a cross-sectional view of the embodiment shown in FIG. 7.
Figure 9:
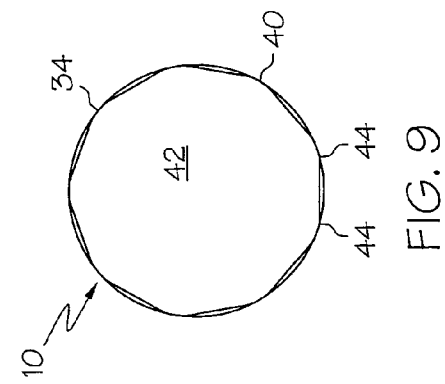
FIG. 9 is a cross-sectional view of an alternative of the embodiment shown in FIG. 7 wherein retaining members are configured to correspond to the circumference of the stent after delivery.

As the shaft 11 is withdrawn, the individual members 40 are disengaged from the shaft 11 thereby allowing the stent 34 to self-expand. As may be seen in FIG. 8, the members 40 are sufficiently long and/or flexible enough to not interfere with the expansion of the stent 34. In some embodiments where the members 40 are configured to stretch elastically as previously described, when shaft 11 is withdrawn during stent delivery, the members 40 may be configured to become a substantially straight member extending from two points on the stent 34 corresponding to ends 44 and 46, such as is shown in FIG. 9. Preferably, ends 44 and 46 are spaced fairly close together along the circumference of stent 34 so that the straightened member 40 would not encroach, or would only minimally encroach, into the interior of the expanded stent 34.

In some embodiments of the invention, members 40 may be constructed from a superelastic or shape-memory material. Some examples of suitable shape-memory materials may include but are not limited to: nitinol, shape-memory polymers and/or superelastic titanium alloys. Where members 40 are made from shape-memory materials the individual members 40 do not appreciably stretch in length, but instead members 40 have the capacity to take one shape when it is looped around the shaft 11 and return to another default shape after the shaft 11 is withdrawn.

Figure 10:
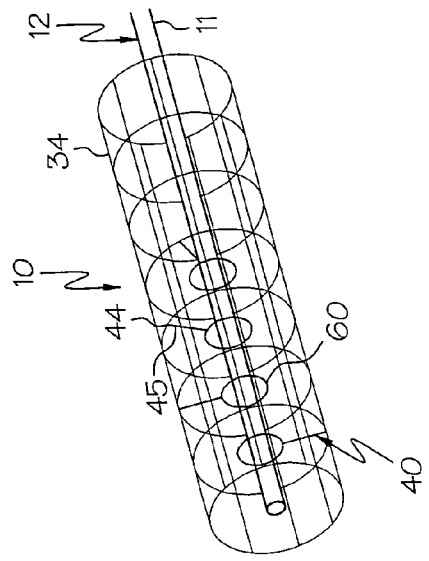
FIG. 10 is a profile view of an embodiment of the invention wherein a stent includes internal members for retaining the stent in a reduced configuration about a shaft of a delivery catheter.
Figure 11:
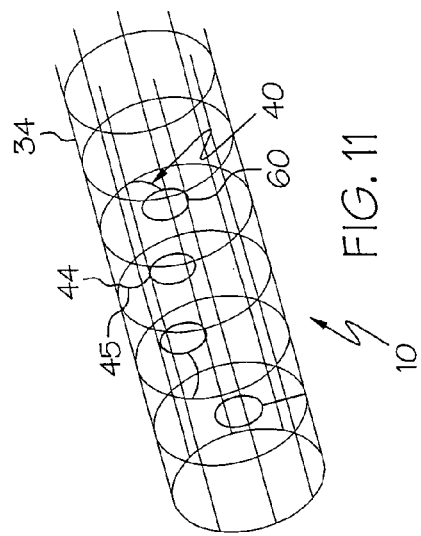
FIG. 11 is a profile view of the embodiment of the invention shown in FIG. 10 wherein following delivery of the stent the retaining members are configured to correspond to the circumference of the stent after delivery.

An example of another configuration of members 40 is shown in FIG. 10 wherein each member 40 has a single extension member 45 extending from end 44 along the circumference of the stent 34. The extension members 45 extend inward into the stent interior 42 to engage the catheter shaft 11 with a shaft engagement member 60. Preferably, shaft engagement member 60 is a hook or ring shaped portion of the member 40 which is engaged to extension member 45. Engagement member 60 may be constructed from the same material or a different material than extension member 45. When the shaft 11 is withdrawn, the members 40 may attain the default shape or may be configured to acquire a new shape wherein the extension members 45 draw the shaft engagement members 60 to a position along the plane of the stent 34 such as is shown in FIG. 11.

In yet another embodiment of the invention shown in FIGS. 12-15, the system 10 is configured to provide a self-expanding stent 34 with the capability of being self-expanded without the need to withdraw the shaft 11 from the stent interior 42 prior to stent delivery. In addition, the stent 34 is retained about the catheter shaft 11 without the use of a retaining sheath, sleeve, or retaining wires as previously discussed.

Figure 12:
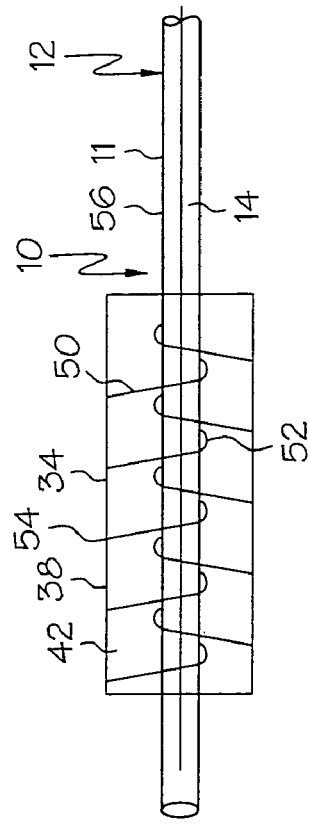
FIG. 12 is a side perspective view of an embodiment of the invention wherein a stent includes internal hooks of shape memory material for retaining the stent in a reduced configuration about a shaft of a delivery catheter.
Figure 13:
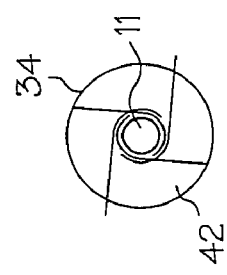
FIG. 13 is a cross-sectional view of the embodiment shown in FIG. 12.

In the embodiment shown in FIGS. 12 and 13 the stent 34 includes at least one, and desirably a plurality, of interior mounted members in the form of hooks, loops or weaves 50. When the stent 34 is held in the reduced profile state prior to delivery, the interior ends 52 of each member 50 are engaged to the catheter shaft 11. As shown in FIG. 12, the ends 52 are preferably partially disposed about the catheter shaft 11. The members may be engaged to the catheter shaft 11, or may be engaged to other members 50 which overlap to retain the stent 34 to the shaft 11 in the unexpanded state.

The exterior end 54 of each member 50 is engaged to one or more struts 38 of stent 34 and restrains the stent from self-expanding. In some embodiments of the invention, the members 50 may be integral with the stent 34 and include ends 52 that are removably engaged to the catheter shaft 11 prior to stent delivery.

Figure 14:
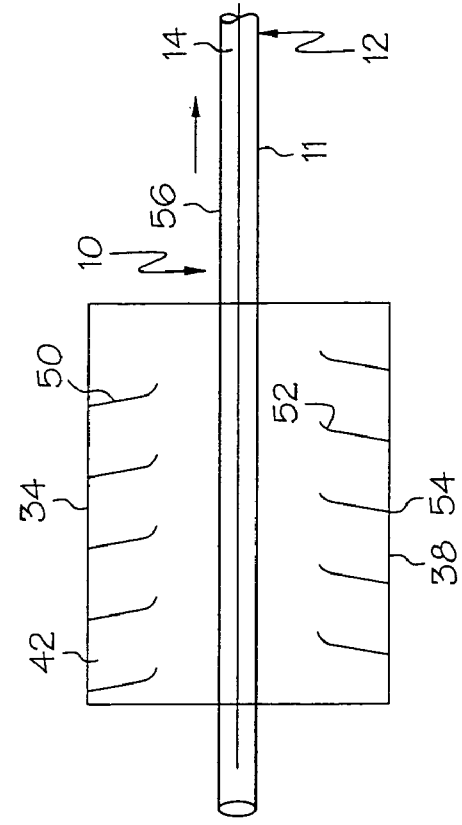
FIG. 14 is a side perspective view of the embodiment shown in FIG. 12, wherein the stent has been expanded by activation of the shape memory hooks which are then disengaged from the catheter shaft thereby releasing the stent to expand.
Figure 15:
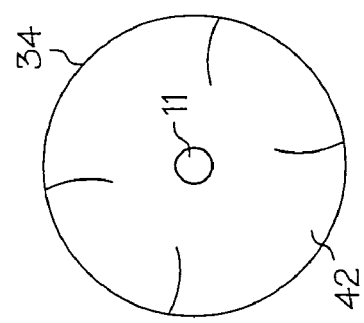
FIG. 15 is a cross-sectional view of the embodiment shown in FIG. 14.

The members 50 are constructed at least partially from a shape memory material. Suitable shape memory materials include any the shape memory materials disclosed above and may be temperature or pH activated. In order to release the stent 34 to self-expand, at least the interior ends 52 of the members 50 are subjected to a change in temperature or pH sufficient to cause the ends 52 to relax their shape and release the stent 34 from the catheter shaft 11 such as is shown in FIGS. 14 and 15. Once the stent is released, the catheter 12 may be withdrawn.

In some embodiments of the invention, the members 50 may be configured to retract into the circumference of the stent thereby ensuring that the members do not extend inward into the stent interior 42 once the stent 34 is fully expanded.

The change in temperature required to cause transformation of the hooks 50 may be accomplished in a variety of ways. In at least one embodiment the shaft 11 defines a lumen 14 through which a wire 56 may be passed. For the purposes of this disclosure, the term wire is includes metal wires, polymer fibers, optical fibers, or other elongate members. In at least one embodiment of the invention, wire 56 may be an optical fiber which is advanced through the shaft 11 to locations adjacent to the hook ends 52. The optical fiber may be used to transmit laser light to the hooks 50 in order to transform the hooks 50 and release the ends 52 from the catheter shaft 11. Alternatively, wire 56 may be a wire or other heating or electrically conductive element which may heat the hooks 50 to release the ends 52 from the shaft 11. In the embodiments where a wire is used to heat the hooks 50, the catheter 12 itself may be a heat conductive wire or material thereby removing the need for lumen 14 and reducing the profile of the catheter 12 further.

In still another embodiment, the lumen 14 may be used to transmit a heated bolus and/or pH-buffered bolus of saline to the stent interior 42 whereupon the increase in temperature and/or pH provided by the bolus causes release of the ends 52 from the shaft. Other methods of providing heat or a change in temperature to the interior of a stent, such as may be known, may also be utilized in the present invention.

It should also be noted that the members 50 may also be constructed to be fixedly engaged to the catheter shaft 11 such that the shape memory aspect of the hooks 50 allows the exterior ends 54 to release the stent struts 38. In such an embodiment the members 50 may be configured to be drawn inward toward the catheter shaft 11 to ensure a reduced profile for retraction of the catheter 12 from the body.

The invention is also directed to methods of securing a medical device such as a stent to a catheter. In accordance with one inventive method, a stent is provided as is a catheter member. The catheter member may be in the form of a tube having a passage therethrough or in the form of a solid member. One or more engagement members, as disclosed above, extends from the stent and is releasably secured to the catheter member.

In accordance with another inventive method, one or more engagement members extending from the catheter member is releasably secured to the stent.

In yet another embodiment of the inventive methods, a stent having one or more flexible members, each having a first end secured to the stent and a second end secured to the stent, is provided. The flexible members form loops. A catheter member is inserted in the loops thereby retaining the stent in the reduced configuration.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A delivery system for delivering an expandable medical device to a body location, the expandable medical device having a reduced configuration and an expanded configuration, the delivery system comprising:
a catheter, the catheter having a catheter shaft having a proximal region and a distal region, the catheter shaft defining a pull-wire lumen, at least a portion of the distal region defining a medical device receiving region;
the expandable medical device disposed about the medical device receiving region in the reduced configuration, the expandable medical device further having proximal and distal device ends;
at least one retractable retaining wire, at least a portion of the at least one retractable retaining wire wound about at least a portion of the expandable medical device and retaining the expandable medical device in the reduced configuration, one end of the at least one retractable retaining wire terminating in at least one pull-wire, the at least one pull-wire extending into the pull-wire lumen to the proximal region of the catheter shaft; and
a portion of the medical device receiving region defining at least one lumen port, the at least one lumen port positioned centrally in the medical device receiving region, the at least one pull-wire extending proximally from the proximal end of the at least one retractable retaining wire and passing through the at least one lumen port to enter into the pull-wire lumen.

2. The delivery system of claim 1 wherein the at least one retractable retaining wire is characterized as one or more ribbons.

3. The delivery system of claim 1 wherein the at least one retractable retaining wire is constructed from a shape memory material.

4. The delivery system of claim 1 wherein the at least one retractable retaining wire is constructed from at least one material of the group consisting of nitinol, acrylate-based polymers, polyurethane-based polymers, polynorbornene-based polymers, polylactide-based polymers, platinum, tungsten, titanium, stainless steel, nickel and any combinations thereof.

5. The delivery system of claim 1 wherein the medical device is a stent.

6. The delivery system of claim 5 wherein the stent comprises a plurality of interconnected struts, the at least one retractable retaining wire being threadingly coiled about selected struts of the stent.

7. The delivery system of claim 1 wherein the medical device receiving region comprises a medical balloon, the delivery system further comprising an inflation lumen, the inflation lumen in fluid communication with the medical balloon.

8. The delivery system of claim 7 wherein the medical device is balloon expandable.

9. The delivery system of claim 1 wherein the at least one retractable retaining wire is constructed and arranged to uncoil from the medical device when the at least one pull-wire is retracted.

10. The delivery system of claim 1 wherein the at least a portion of the at least one retractable retaining wire comprises at least two branches, the at least two branches comprising a proximal branch and a distal branch, the proximal branch being wound about at least a proximal portion of the expandable medical device in the reduced state and the distal branch being wound about at least a distal portion of the expandable medical device in the reduced state.

11. The delivery system of claim 10 wherein the at least one pull-wire comprises a proximal branch pull-wire and a distal branch pull-wire, the one end of the proximal branch terminating in the proximal branch pull-wire and the at one end of the distal branch terminating at the distal branch pull-wire.

12. The delivery system of claim 11 wherein the proximal branch and the distal branch are independently retractable.

13. The delivery system of claim 11 wherein the at least one pull-wire is a single pull-wire, the one end of the proximal branch and the distal branch terminating in the single pull-wire.

* * * * *